United States Patent
Zhang

(10) Patent No.: US 12,064,351 B2
(45) Date of Patent: Aug. 20, 2024

(54) CARTILAGE SUBSTITUTE

(71) Applicant: Beijing AK Medical Co., Ltd., Beijing (CN)

(72) Inventor: Weiping Zhang, Beijing (CN)

(73) Assignee: Beijing AK Medical Co., Ltd., Beijing (CN)

( * ) Notice: Subject to any disclaimer, the term of this patent is extended or adjusted under 35 U.S.C. 154(b) by 337 days.

(21) Appl. No.: 16/957,123

(22) PCT Filed: Apr. 4, 2019

(86) PCT No.: PCT/CN2019/081493
§ 371 (c)(1),
(2) Date: Jun. 23, 2020

(87) PCT Pub. No.: WO2020/155375
PCT Pub. Date: Aug. 6, 2020

(65) Prior Publication Data
US 2021/0361435 A1 Nov. 25, 2021

(30) Foreign Application Priority Data

Feb. 1, 2019 (CN) .......................... 201910105632.7

(51) Int. Cl.
*A61F 2/30* (2006.01)
(52) U.S. Cl.
CPC ........ *A61F 2/30756* (2013.01); *A61F 2/3094* (2013.01); *A61F 2002/30224* (2013.01);
(Continued)
(58) Field of Classification Search
CPC ................ A61F 2/3094; A61F 2/30756; A61F 2002/30581; A61F 2/28; A61F 2/30;
(Continued)

(56) References Cited

U.S. PATENT DOCUMENTS

| 4,834,757 A * | 5/1989 | Brantigan ................. A61F 2/42 |
| | | 623/17.11 |
| 8,828,088 B2 | 9/2014 | Linares |

(Continued)

FOREIGN PATENT DOCUMENTS

| CN | 101883542 A | 11/2010 |
| CN | 103920190 A | 7/2014 |

(Continued)

OTHER PUBLICATIONS

The extended European search report of the corresponding EP patent application No. 19912624.4, mail date Nov. 9, 2021.

*Primary Examiner* — Christopher D. Prone
(74) *Attorney, Agent, or Firm* — Samson G. Yu

(57) ABSTRACT

The disclosure provides a cartilage substitute, which includes at least one cartilage unit, the cartilage unit including: a base, including a subcutaneous layer portion forming contact friction with a corresponding skeleton, a deep layer area portion contacting with a target skeleton and an intermediate layer portion provided between the subcutaneous layer portion and the deep layer area portion. A fluid storage cavity is disposed in the subcutaneous layer portion. A first communicating passage is disposed in the subcutaneous layer portion. A second communicating passage is disposed in the intermediate layer portion, a third communicating passage is disposed in the deep layer area portion. The fluid storage cavity, the second communicating passage and the third communicating passage are disposed to gradually increase hardness of the subcutaneous layer portion, the intermediate layer portion and the deep layer area portion.

7 Claims, 6 Drawing Sheets

(52) U.S. Cl.
CPC .............. *A61F 2002/30291* (2013.01); *A61F 2002/30317* (2013.01); *A61F 2002/30581* (2013.01); *A61F 2002/30673* (2013.01); *A61F 2002/3097* (2013.01)

(58) Field of Classification Search
CPC ...... A61F 2002/2835; A61F 2002/2839; A61F 2002/30317
See application file for complete search history.

(56) References Cited

U.S. PATENT DOCUMENTS

| | | |
|---|---|---|
| 9,168,144 B2 | 10/2015 | Rivin et al. |
| 2005/0177238 A1* | 8/2005 | Khandkar ........... A61L 27/3856 623/23.57 |
| 2009/0012615 A1 | 1/2009 | Fell |
| 2009/0125108 A1 | 5/2009 | Linares |
| 2019/0015211 A1 | 1/2019 | Myung et al. |

FOREIGN PATENT DOCUMENTS

| | | |
|---|---|---|
| CN | 204971713 U | 1/2016 |
| CN | 109528358 A | 3/2019 |

* cited by examiner

CARTILAGE SUBSTITUTE

CROSS-REFERENCE TO RELATED APPLICATION(S)

The present application claims priority to Chinese Patent Application No. 201910105632.7, filed on Feb. 1, 2019 and entitled "Cartilage Substitute", the contents of which are hereby incorporated by reference in its entirety.

TECHNICAL FIELD

The disclosure relates to a field of artificial prostheses, and particularly to a cartilage substitute.

BACKGROUND

Articular cartilage is an important part of a joint. Since an articular cartilage has certain viscoelasticity and pressure resistance and can reduce frictions, bear loads and absorb shocks, integrity of the articular cartilage is very important to joint motions. Articular cartilage injury is a common disease that may occur at any age and gender. Articular cartilages may be injured by articular metamorphosis and wounds, and various metabolic factors such as diabetes, obesity and fondness of liquor and mechanical factors such as joint instability, wounds and dislocation may all cause articular cartilage injuries. The articular cartilage, a connective tissue lack of blood supply, is unlikely to be repaired and regenerated in a late injury period, and hardly heals if being injured or having a lesion to further cause joint damage. How to repair articular cartilage defects has always been a puzzling problem of the medical field for a long time. At present, some non-operative treatment methods such as weight control, proper motion restriction, drug treatment, anti-inflammation analgesia and intra-articular injection of corticosteroids and hyaluronate are adopted. By these methods, pains may be alleviated to a certain extent, but cartilage repair effects are not so obvious, and the drug treatment method is obviously limited and required to consider risks such as drug reaction, joint infection and systemic response. An autologous or allogeneic cartilage grafting method is also adopted for clinical treatment. Autologous cartilage grafting is greatly limited due to limited sources of cartilage tissues. Allogeneic cartilage grafting has the risk of immunological rejection or even disease spreading. Under the condition that symptoms of the articular cartilage may not be relieved by conservative treatment, operative treatment methods such as joint replacement may also be selected. In addition, the medical field has been committed to seeking for and trying to use proper materials for cartilage substitution to avoid premature joint replacement.

At present, although the viscoelasticity of a human cartilage is clinically imitated through an artificial cartilage such as a porous structure, a substitute of a porous structure is still greatly different from a cartilage of a patient, may not actually recover mechanical characteristics and friction characteristics of the human physiological cartilage and may not achieve an ideal matching degree, which may undoubtedly change a friction environment of an articular surface in a normal state, thereby increasing wear to the cartilage opposite to the cartilage substitute material to cause secondary injury to the patient.

SUMMARY

The disclosure is intended to provide a cartilage substitute, to solve the problem in a conventional art that an artificial cartilage may not actually recover characteristics of a human physiological cartilage and is low in matching degree with a cartilage of a patient and likely to cause secondary injury to the patient.

According to an aspect of the disclosure, a cartilage substitute is provided, which is implantable into a target skeleton, the target skeleton being cooperated with a corresponding skeleton, the cartilage substitute including at least one cartilage unit, the cartilage unit including: a base, including a subcutaneous layer portion forming contact friction with the corresponding skeleton, a deep layer area portion contacting with the target skeleton and an intermediate layer portion provided between the subcutaneous layer portion and the deep layer area portion, a first opening being formed in an outer surface of the subcutaneous layer portion and a second opening being formed in an inner surface of the deep layer area portion; a fluid storage cavity, disposed in the subcutaneous layer portion and communicated with the first opening and the second opening respectively, a fluid being capable of being stored in the fluid storage cavity and flowing out of the base through the first opening and the second opening; a first communicating passage, disposed in the subcutaneous layer portion and communicating the fluid storage cavity and the first opening; and a second communicating passage and third communicating passage, communicating the fluid storage cavity and the second opening, the second communicating passage being disposed in the intermediate layer portion, the third communicating passage being disposed in the deep layer area portion and a density of the second communicating passage being higher than a density of the third communicating passage, wherein the fluid storage cavity, the second communicating passage and the third communicating passage are disposed to make a hardness of the subcutaneous layer portion lower than a hardness of the intermediate layer portion and make the hardness of the intermediate layer portion lower than a hardness of the deep layer area portion.

In some embodiments, a fourth communicating passage is disposed in the subcutaneous layer portion, and two fluid storage cavities of two adjacent cartilage units are communicated through the fourth communicating passage.

In some embodiments, a cross section of the fourth communicating passage is an ellipse, and an extending direction of a short axis of the ellipse is parallel to a superimposition direction of the subcutaneous layer portion, the intermediate layer portion and the deep layer area portion.

In some embodiments, an accommodation pool is disposed at the first opening, the first communicating passage communicates the accommodation pool and the fluid storage cavity, and a diameter of the first communicating passage is smaller than a diameter of the first opening.

In some embodiments, the accommodation pool is of a funnel shaped or a bowl shaped.

In some embodiments, the first communicating passage and/or the second communicating passage and/or the third communicating passage are/is of straight cylinder shaped.

In some embodiments, the first communicating passage and/or the second communicating passage and/or the third communicating passage are/is of spiral shaped.

In some embodiments, the cartilage substitute includes multiple cartilage units disposed in an array, multiple subcutaneous layer portions of multiple of cartilage units form a subcutaneous layer of the cartilage substitute, multiple deep layer area portions of multiple of cartilage units form a deep layer area of the cartilage substitute, multiple intermediate layer portions of multiple of cartilage units form an intermediate layer of the cartilage substitute, multiple fluid storage cavities of multiple of cartilage units are divided into multiple layers in the subcutaneous layer, and the fluid storage cavities of two adjacent layers are staggered.

In some embodiments, the base is made from a transparent material, and the fluid storage cavity, the first communicating passage, the second communicating passage and the third communicating passage are formed by femtosecond laser engraving.

In some embodiments, the base is made from an elastic polymer material.

With adoption of the technical solution of the disclosure, the fluid storage cavity, the second communicating passage and the third communicating passage are disposed to make the hardness of the subcutaneous layer portion lower than the hardness of the intermediate layer portion and make the hardness of the intermediate layer portion lower than the hardness of the deep layer area portion, so that a mechanical characteristic distribution of the cartilage substitute is closer to a human physiological cartilage, adaptability between the cartilage substitute and a human physiological skeleton is improved, and wear to the cartilage substitute and the skeleton corresponding to the cartilage substitute is reduced. In addition, when a patient moves, a joint squeezes the cartilage substitute, then the fluid storage cavity forms a structure like a pump, and a synovial fluid in an articular capsule may be pumped to an articular surface for lubrication through the first communicating passage, the second communicating passage and the third communicating passage, so that wear is further reduced.

BRIEF DESCRIPTION OF THE DRAWINGS

The drawings forming a part of the application in the specification are adopted to provide a further understanding to the disclosure. Schematic embodiments of the disclosure and descriptions thereof are adopted to explain the disclosure and not intended to form improper limits to the disclosure. In the drawings.

Figure 1:
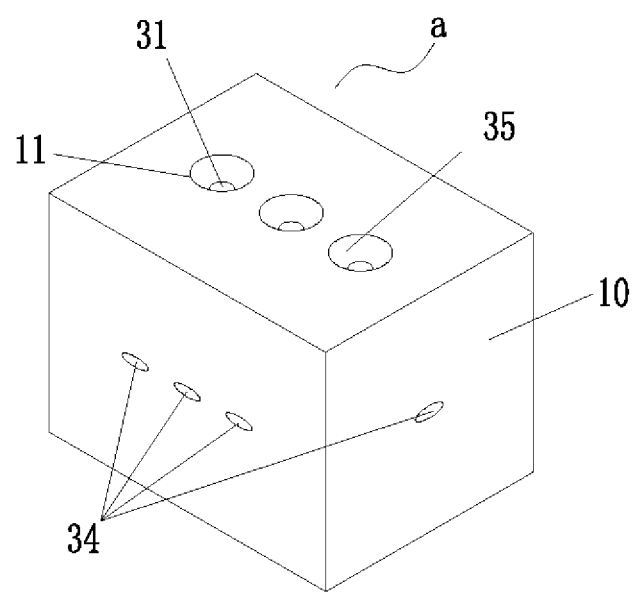
FIG. 1 is a structure diagram of a cartilage unit of a cartilage substitute according to embodiment 1 of the disclosure.

Herein, the drawings include the following drawing reference signs:

A: cartilage substitute; a: cartilage unit; X: subcutaneous layer; Y: intermediate layer; Z: deep layer area; 10: base; 11: first opening; 12: second opening; 20: fluid storage cavity; 31: first communicating passage; 32: second communicating passage; 33: third communicating passage; 34: fourth communication passage; 35: accommodation pool; and 40: support portion.

DETAILED DESCRIPTION OF THE EMBODIMENTS

It is to be noted that the embodiments in the application and characteristics in the embodiments may be combined without conflicts. The disclosure will be described below with reference to the drawings and in combination with the embodiments in detail.

A human physiological cartilage includes a large number of collagen fibers, the cartilage may be divided into a subcutaneous layer, a transitional layer (or called an intermediate layer), a deep layer and a calcified cartilage layer according to different arrangement manners of the collagen fibers, and mechanical characteristics of each layer make functions of each layer different. Most of the cartilage cell collagen fibers of the subcutaneous layer are disposed in parallel with an articular surface, and mainly act to resist shearing forces. The collagen fibers of the transitional layer (intermediate layer) are disposed according to random directions and rules, and mainly act to resist pressure. The collagen fibers of a deep layer area are disposed in a direction perpendicular to the articular surface, and resist both of the shearing forces and the pressure. The calcified cartilage layer acts for transition and load transmission from a cartilage layer to a subchondral bone and distribution of various mechanical loads on the articular surface to bones under the cartilage. Hardness of the physiological cartilage is sequentially increased from superficial to deep layers, and viscoelasticity of each layer is also greatly different.

As shown in FIG. 1 to FIG. 4, a cartilage substitute of an embodiment may be implanted into a target skeleton such as a femoral head and a femoral condyle, and is cooperated with a corresponding skeleton corresponding to an acetabular bone and a tibial plateau to realize a joint function. The cartilage substitute includes at least one cartilage unit a. The cartilage unit a includes a base 10, a fluid storage cavity 20, a first communicating passage 31, a second communicating passage 32 and a third communicating passage 33. Herein, the base 10 includes a subcutaneous layer portion forming contact friction with the corresponding skeleton, a deep layer area portion contacting with the target skeleton and an intermediate layer portion disposed between the subcutaneous layer portion and the deep layer area portion. A first opening 11 is formed in an outer surface of the subcutaneous layer portion. A second opening 12 is formed in an inner surface of the deep layer area portion. The fluid storage cavity 20 is disposed in the subcutaneous layer portion, and is communicated with the first opening 11 and the second opening 12 respectively. A fluid may be stored in the fluid storage cavity 20 and flow out of the base 10 through the first opening 11 and the second opening 12. The first communicating passage 31 is disposed in the subcutaneous layer portion, and communicates the fluid storage cavity 20 and the first opening 11. The second communicating passage 32 and the third communicating passage 33 communicate the fluid storage cavity 20 and the second opening 12. The second communicating passage 32 is disposed in the intermediate layer portion. The third communicating passage 33 is disposed in the deep layer area portion. A density of the second communicating passage 32 is higher than a density of the third communicating passage 33. It is to be noted that the "inner surface" and the "outer surface" are of the base 10 relative to the target skeleton, namely the side, contacting with the target skeleton, of the base 10 is an "inner" side and the side far away from the target skeleton is an "outer" side.

With adoption of the technical solution of the embodiment, the fluid storage cavity 20, the second communicating passage 32 and the third communicating passage 33 are disposed to make the hardness of the subcutaneous layer portion lower than the hardness of the intermediate layer portion and make the hardness of the intermediate layer portion lower than the hardness of the deep layer area portion, so that a mechanical characteristic distribution of the cartilage substitute is closer to a human physiological cartilage, adaptability between the cartilage substitute and a human physiological skeleton is improved, and wear to the cartilage substitute and the skeleton corresponding to the cartilage substitute is reduced. In addition, when a patient moves, a joint squeezes the cartilage substitute, then the fluid storage cavity 20 forms a structure like a pump, and a synovial fluid in an articular capsule may be pumped to an articular surface for lubrication through the first communicating passage 31, the second communicating passage 32 and the third communicating passage 33, so that wear is further reduced.

Figure 4:
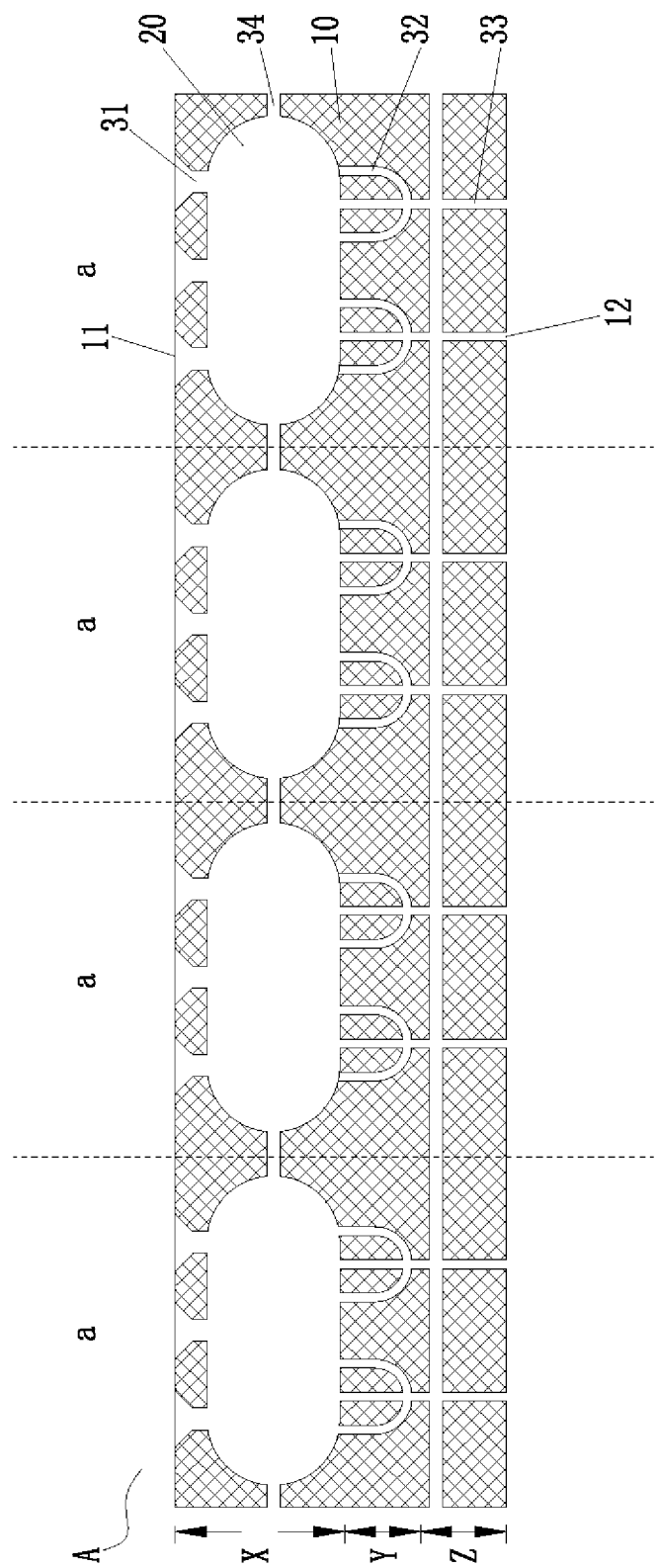
FIG. 4 is a sectional structure diagram of a cartilage substitute formed by the cartilage unit in FIG. 1.

As shown in FIG. 4, the cartilage substitute A includes multiple cartilage units a disposed in an array, multiple subcutaneous layer portions form a subcutaneous layer X of the cartilage substitute, multiple deep layer area portions form a deep layer area Z of the cartilage substitute, and multiple intermediate layer portions form an intermediate layer Y of the cartilage substitute. According to the cartilage substitute of the embodiment, sizes of the fluid storage cavities 20 and diameters and distribution densities of the communicating passages in each layer are controlled to control hardness and viscoelasticity of each layer to make hardness and elasticity of each portion of the cartilage substitute A close to a hardness and elasticity distribution of the human physiological cartilage.

Preferably, the base 10 of the embodiment is a transparent medical polyurethane material, and shore hardness thereof is about 50A to 90A, slightly higher than the human physiological articular cartilage. The polyurethane material has high flexibility and wear resistance as well as excellent performance such as high toughness, solvent resistance, hydrolysis resistance, microorganism resistance, wear resistance and flexing resistance, and the fluid storage cavity 20, the first communicating passage 31, the second communicating passage 32, the third communicating passage 33 and the like may be formed by femtosecond laser engraving in the polyurethane material. In another embodiment, the base may also be made from polyethylene, polytetrafluoroethylene, silica gel and the like.

As shown in FIG. 1 to FIG. 4, in the embodiment, a fourth communicating passage 34 is disposed in the subcutaneous layer portion, and two fluid storage cavities 20 of two adjacent cartilage units are communicated through the fourth communicating passage 34. The fourth communicating passage 34 makes the synovial fluid in each fluid storage cavity 20 relatively uniform and further make a fluid film formed on the articular surface by the synovial fluid uniform in thickness to ensure a lubrication effect.

In the embodiment, the first communicating passage 31, the second communicating passage 32, the third communicating passage 33 and the fourth communicating passage 34 are substantially straight cylinder shape tubes, and such a tube structure is regular in shape and easy to make.

Figure 2:
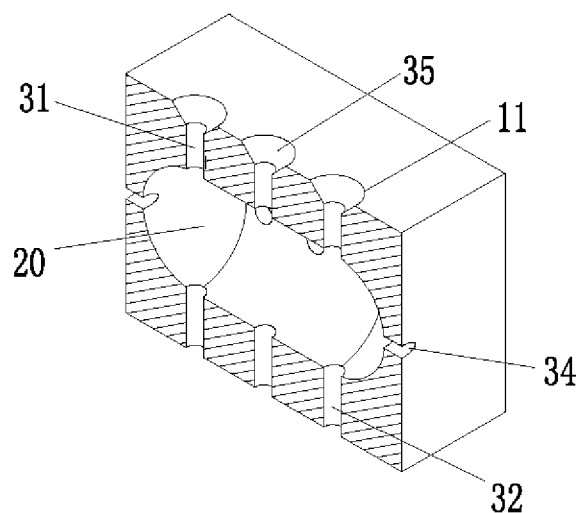
FIG. 2 is a structure diagram of the cartilage unit in FIG. 1 at a section angle.
Figure 3:
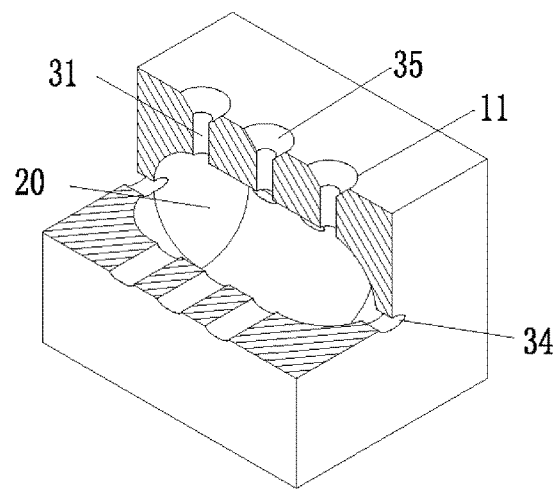
FIG. 3 is a structure diagram of the cartilage unit in FIG. 1 at another section angle.

Preferably, as shown in FIG. 1 to FIG. 3, in the embodiment, a cross section of the fourth communicating passage 34 is an ellipse, and an extending direction of a short axis of the ellipse is parallel to a superimposition direction of the subcutaneous layer portion, the intermediate layer portion and the deep layer area portion. Then, when limbs of the patient move, articular surfaces are mutually compressed or released by relative movements between the skeletons to elastically deform the cartilage substitute A. When a compressive force is applied to the articular surface, the fourth communicating passage 34 may be pressurized and closed, which is favorable for slow discharge of the articular synovial fluid in the elastic polyurethane from the first communicating passage 31 to the articular surface. After the compressive force is released, the fourth communicating passage 34 may be opened, the size of the elastic polyurethane is enlarged and the synovial fluid is sucked into the fluid storage cavity 20 and the communicating passage of each layer again. In such cycles, the articular synovial fluid may be continuously supplemented to the articular friction surface to improve a lubrication environment of the articular surface.

A volume of the fluid storage cavity 20 and a ratio between the fluid storage cavity 20 and a sum of cross sectional areas of the communicating passages of each layer may be regulated to achieve different strain rates of the polyurethane material, and changing arrangement densities of the communicating passages of each layer and designing different cross sectional shapes and diameters of the communicating passages may also achieve different hardness and strain rates of the polyurethane material, thereby making the polyurethane material closer to the viscoelasticity of the physiological cartilage.

Furthermore, as shown in FIG. 1, in the embodiment, an accommodation pool 35 is disposed at the first opening 11, the first communicating passage 31 communicates the accommodation pool 35 and the fluid storage cavity 20, and a diameter of the first communicating passage 31 is smaller than a diameter of the first opening 11. In an unloaded state of the articular surface, the accommodation pool may be filled with the synovial fluid; and when the articular surface is loaded and squeezed, part of the synovial fluid in the accommodation pool is squeezed into the first communicating passage 31 and the fluid storage cavity 20, but a considerable amount of synovial fluid may not be timely squeezed back into the first communicating passage 31 and is diffused into a peripheral articular friction surface along an outlet edge of the accommodation pool 35 under the action of positive pressure because an aperture of the accommodation pool 35 is larger than an aperture of the first communicating passage 31, so that the synovial fluid may be effectively supplemented in the friction surface, and the lubrication state of the articular surface is greatly improved.

Specifically, the accommodation pool 35 is of a funnel shaped in the embodiment, and in another embodiment, the accommodation pool may also be in another shape capable of storing the fluid such as a bowl shaped.

Figure 5:
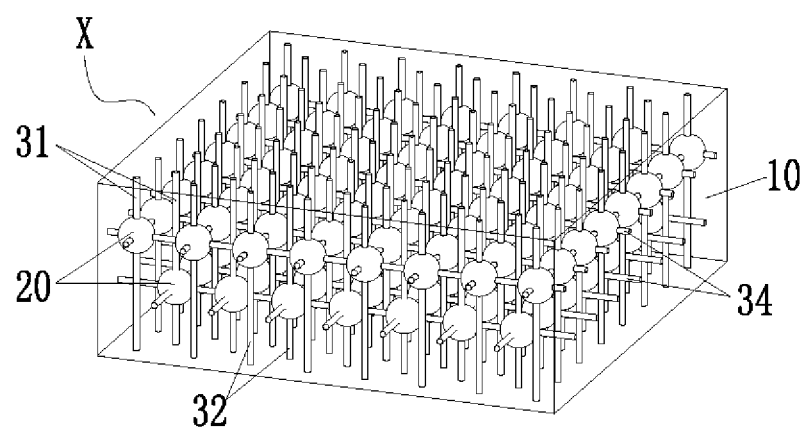
FIG. 5 is a structure diagram of a cartilage substitute according to embodiment 2 of the disclosure.

For the cartilage substitute according to embodiment 2, an arrangement manner for the fluid storage cavity 20 is regulated on the basis of embodiment 1. As shown in FIG. 5, the cartilage substitute A of the embodiment includes multiple cartilage units a disposed in an array, multiple subcutaneous layer portions form a subcutaneous layer X of the cartilage substitute, multiple deep layer area portions form a deep layer area of the cartilage substitute, multiple intermediate layer portions form an intermediate layer of the cartilage substitute, fluid storage cavities 20 are divided into multiple layers in the subcutaneous layer X, and the fluid storage cavities 20 of two adjacent layers are staggered. Herein, staggering refers to that projections of the fluid storage cavity 20 disposed at a lower layer and the fluid storage cavity 20 disposed at an adjacent upper layer are not completely overlapped in the superimposition direction. It can be understood that not complete overlapping may refer to partial overlapping and may also refer to complete non-overlapping.

Figure 6:
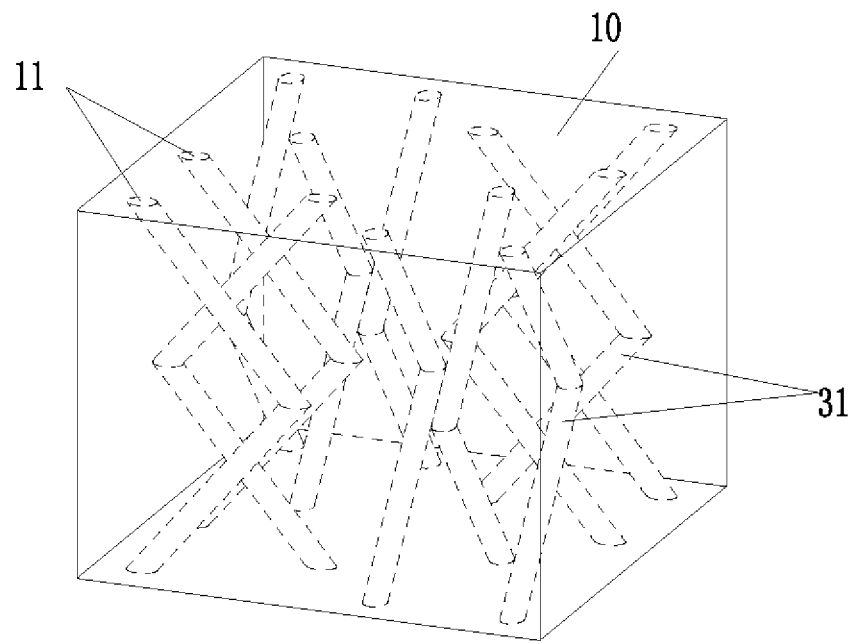
FIG. 6 is a structure diagram of a cartilage unit of a cartilage substitute according to embodiment 3 of the disclosure.

For the cartilage substitute according to embodiment 3, shapes of the communicating passages are regulated on the basis of embodiment 1. As shown in FIG. 6, each first communicating passage 31 of the embodiment is formed by connecting two sections of straight cylinder shape passages forming an angle. In such a manner, functions of communication and elasticity regulation may also be realized, and meanwhile, an injection angle may be provided for the synovial fluid. Each of the second communicating passage and/or third communicating passage not presented in the figure may also be such a communicating passage formed by connecting two sections of straight cylinder shape passages forming an angle.

Figure 7:
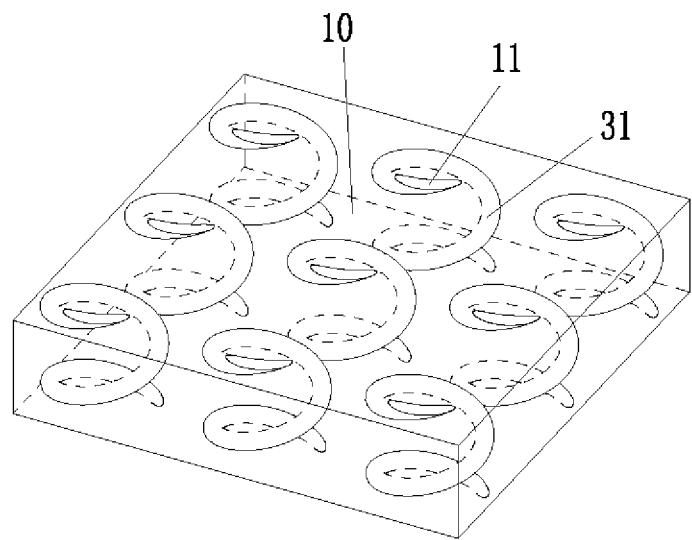
FIG. 7 is a structure diagram of a cartilage unit of a cartilage substitute according to embodiment 4 of the disclosure.

For the cartilage substitute according to embodiment 4, the shapes of the communicating passages are regulated on the basis of embodiment 1. As shown in FIG. 7, the first communicating passage 31 of the embodiment is of spiral shaped. In such a manner, the functions of communication and elasticity regulation may also be realized. Each of the second communicating passage and/or third communicating passage not presented in the figure may also be such a spiral shape communicating passage.

Figure 8:
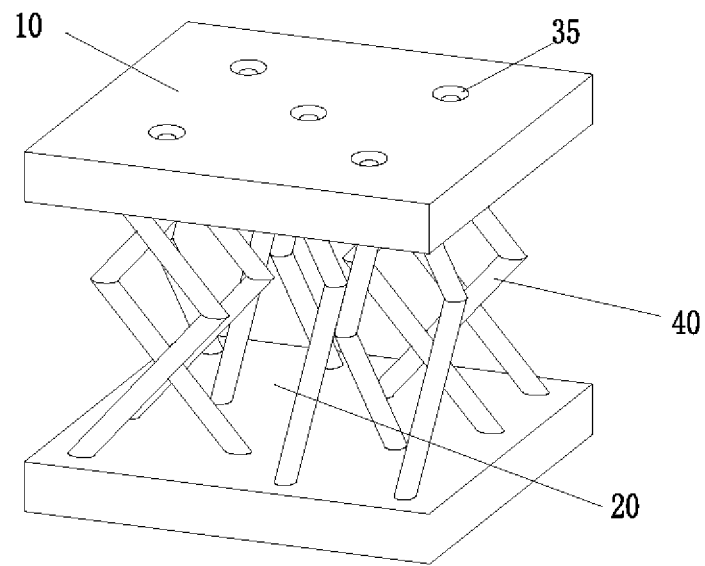
FIG. 8 is a structure diagram of a cartilage unit of a cartilage substitute according to embodiment 5 of the disclosure.
Figure 9:
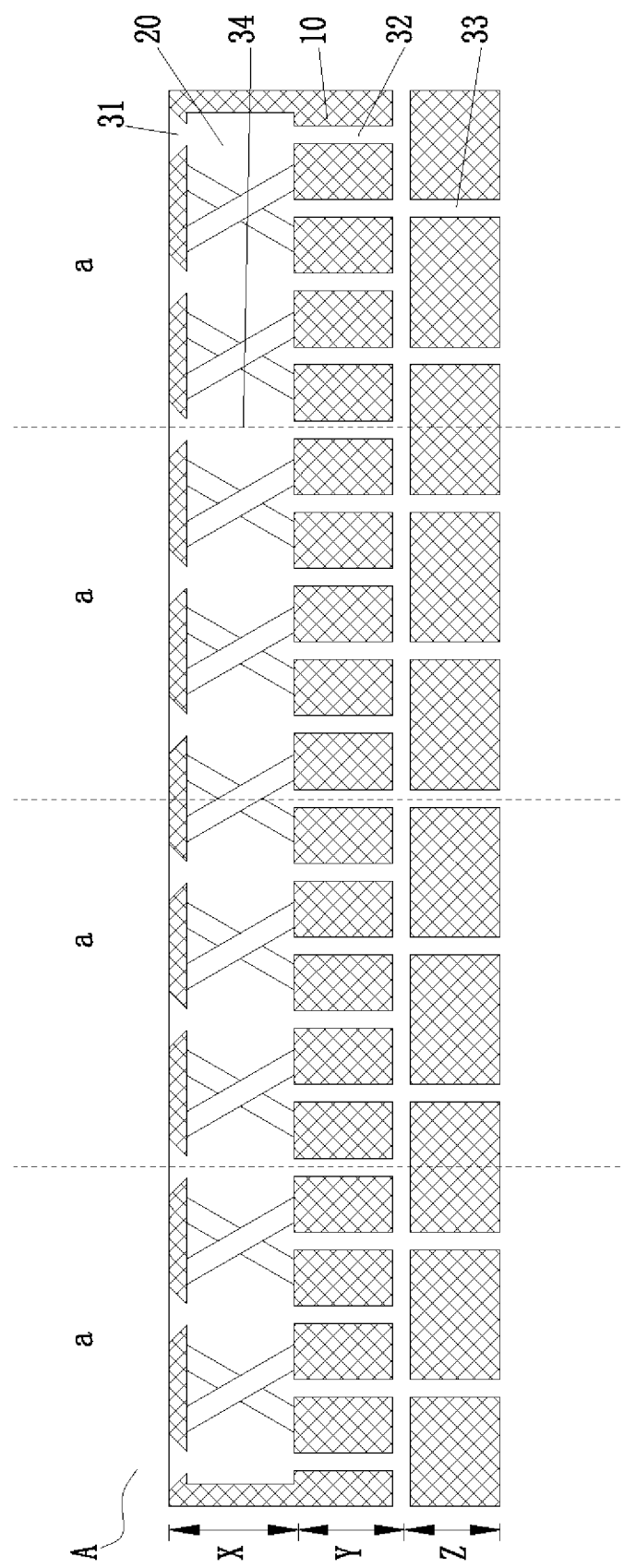
FIG. 9 is a sectional structure diagram of a cartilage substitute formed by the cartilage unit in FIG. 8.

For the cartilage substitute according to embodiment 5, forming manners for the communicating passages and the fluid storage cavity are regulated on the basis of embodiment 1. As shown in FIG. 8 and FIG. 9, multiple support portions 40 are formed in the base of the cartilage substitute of the embodiment by use of a femtosecond technology, and spaces between each support portions 40 form the fluid storage cavity 20 and the first communicating passage communicated with the accommodation pool 35.

During practical use, the cartilage substitute of each abovementioned embodiment may be cut or prefabricated into a proper shape and disposed at a physiological cartilage defect part to be substituted. Since the fluid storage cavity and each communicating passage are continuously disposed in an array, an open passage exposed into the articular capsule is formed at a shape boundary of the cartilage substitute, which is favorable for charging and discharging the synovial fluid for supplementation.

From the above description, it can be seen that the abovementioned embodiments of the disclosure have the following technical effects.

The fluid storage cavity, the second communicating passage and the third communicating passage are disposed to make the hardness of the subcutaneous layer portion lower than the hardness of the intermediate layer portion and make the hardness of the intermediate layer portion lower than the hardness of the deep layer area portion, so that a mechanical characteristic distribution of the cartilage substitute is closer to a human physiological cartilage, adaptability between the cartilage substitute and a human physiological skeleton is improved, and wear to the cartilage substitute and the skeleton corresponding to the cartilage substitute is reduced. In addition, when the patient moves, the joint squeezes the cartilage substitute, then the fluid storage cavity forms a structure like a pump, and a synovial fluid in the articular capsule may be pumped to the articular surface for lubrication through the first communicating passage, the second communicating passage and the third communicating passage, so that wear is further reduced.

The above is only the preferred embodiment of the disclosure and not intended to limit the disclosure. For those skilled in the art, the disclosure may have various modifications and variations. Any modifications, equivalent replacements, improvements and the like made within the spirit and principle of the disclosure shall fall within the scope of protection of the disclosure.

What is claimed is:

1. A cartilage substitute, implantable into a first bone, the first bone being cooperated with a second bone to form a joint, the cartilage substitute comprising at least one cartilage unit, the cartilage unit comprising:
    a base, comprising a subcutaneous layer forming contact friction with the second bone, a deep layer contacting with the first bone and an intermediate layer disposed between the subcutaneous layer and the deep layer, a first opening being formed in an outer surface of the subcutaneous layer and a second opening being formed in an inner surface of the deep layer;
    a fluid storage cavity, disposed in the subcutaneous layer and communicated with the first opening and the second opening respectively, a fluid being capable of being stored in the fluid storage cavity and flowing out of the base through the first opening and the second opening;
    a first communicating passage, disposed in the subcutaneous layer and communicating the fluid storage cavity and the first opening; and
    a second communicating passage and third communicating passage, communicating the fluid storage cavity and the second opening, the second communicating passage being disposed in the intermediate layer, the third communicating passage being disposed in the deep layer and a distribution density of the intermediate layer being higher than a distribution density of the deep layer,
    wherein the fluid storage cavity, the second communicating passage and the third communicating passage are disposed to make a pressure resistance of the subcutaneous layer lower than a pressure resistance of the intermediate layer and make the pressure resistance of the intermediate layer lower than a pressure resistance of the deep layer;
    wherein the first communicating passage and/or the second communicating passage and/or the third communicating passage are/is of spiral shaped.

2. The cartilage substitute as claimed in claim 1, wherein a fourth communicating passage is disposed in the subcutaneous layer position, there are a plurality of cartilage units, and two fluid storage cavities of two adjacent cartilage units of the plurality of cartilage units are communicated through the fourth communicating passage.

3. The cartilage substitute as claimed in claim 2, wherein a cross section of the fourth communicating passage is an ellipse, and an extending direction of a short axis of the ellipse is parallel to a superimposition direction of the subcutaneous layer, the intermediate layer and the deep layer.

4. The cartilage substitute as claimed in claim 1, wherein an accommodation pool is disposed at the first opening, the first communicating passage communicates the accommodation pool and the fluid storage cavity, and a diameter of the first communicating passage is smaller than a diameter of the first opening.

5. The cartilage substitute as claimed in claim 4, wherein the accommodation pool is of a funnel shaped or a bowl shaped.

6. The cartilage substitute as claimed in claim 1, wherein the base is made from a transparent material, and the fluid storage cavity, the first communicating passage, the second communicating passage and the third communicating passage are formed by femtosecond laser engraving.

7. The cartilage substitute as claimed in claim 1, wherein the base is made from an elastic polymer material.

\* \* \* \* \*